United States Patent [19]
Overend

[11] 3,930,506
[45] Jan. 6, 1976

[54] DISPOSABLE PHLEBOTOMIST'S TOURNIQUET

[76] Inventor: Thomas F. Overend, 4379 Dart Ave., Minneapolis, Minn. 55424

[22] Filed: June 3, 1974

[21] Appl. No.: 475,452

[52] U.S. Cl. .............................................. 128/327
[51] Int. Cl.² ............................................. A61B 17/12
[58] Field of Search ........................... 128/325–327, 128/155–157, 165, 169, 170–171, 168, 76 R; 24/16 R, 16 PB, 17 R, 17 A, DIG. 11, DIG. 18

[56] References Cited
UNITED STATES PATENTS

| 1,885,007 | 10/1932 | Rosenblatt | 128/327 X |
| 2,703,083 | 3/1955 | Gross | 128/156 |
| 3,086,529 | 4/1963 | Munz et al. | 128/327 |
| 3,233,608 | 2/1966 | Scaler, Jr. | 128/169 |
| 3,504,675 | 4/1970 | Bishop, Jr. | 128/327 |
| 3,587,584 | 6/1971 | Keller | 128/327 |

*Primary Examiner*—Robert W. Michell
*Assistant Examiner*—Rick Opitz
*Attorney, Agent, or Firm*—James R. Haller; H. Dale Palmatier

[57] ABSTRACT

A disposable phlebotomist's tourniquet comprising a flat solid, elastic band of a length sufficient, when stretched, to encircle the human upper arm and including adjacent one end a relatively non-stretchable pressure-sensitive adhesive strip protectively covered for storage by a protective liner of treated paper or the like having one end projecting beyond the end of the adhesive strip as a graspable pull tab so that the liner may be pulled away.

7 Claims, 5 Drawing Figures

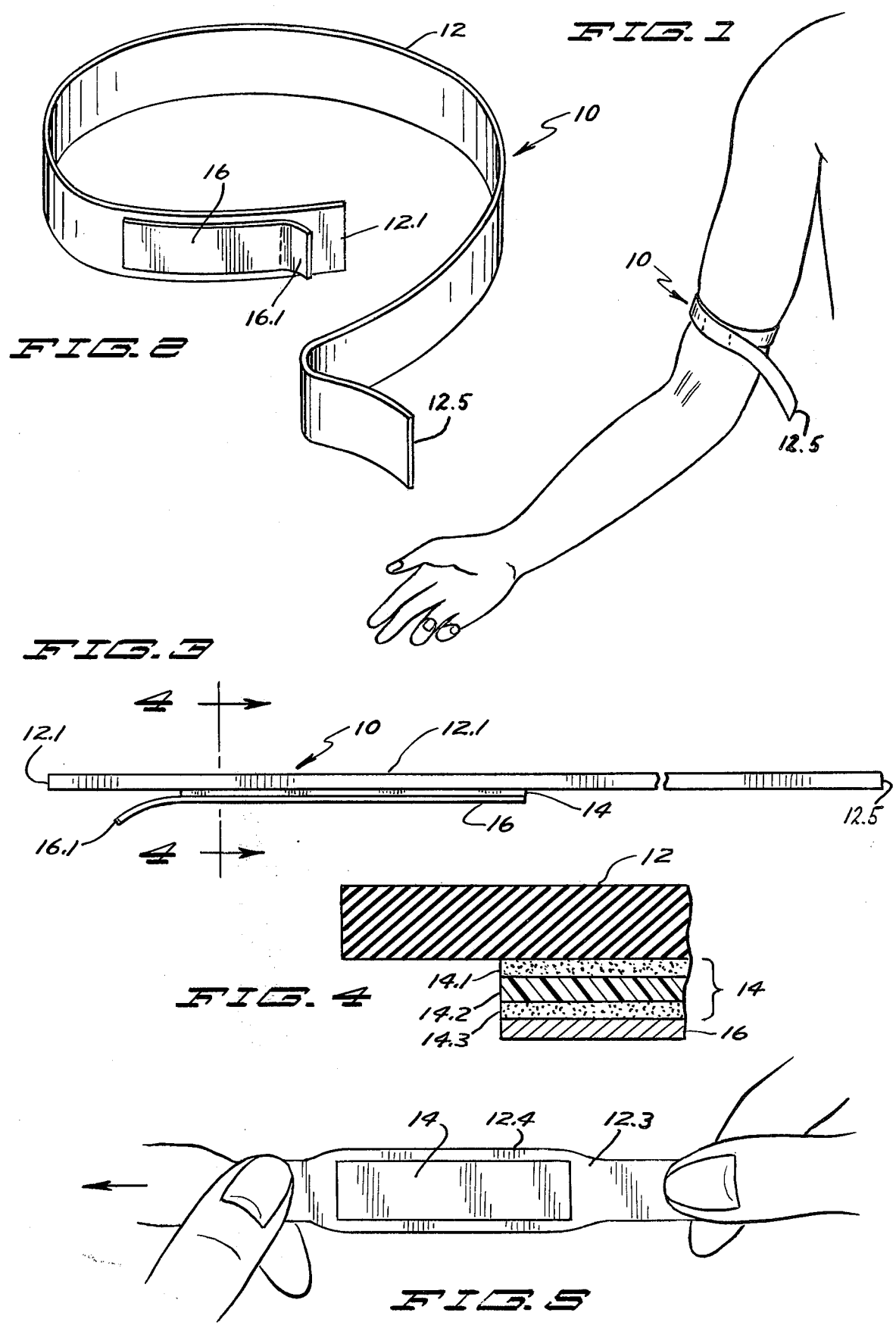

DISPOSABLE PHLEBOTOMIST'S TOURNIQUET

BACKGROUND OF THE INVENTION

In hospitals and doctors' offices, blood samples are often taken from a person's arm so that various blood tests can be performed. To obtain a blood sample, the medical technician ("phlebotomist" herein) will ordinarily wrap a tourniquet about the patient's upper arm to cause veins in the distal portion of the arm to stand out, whereupon blood can be removed by means of a needle and syringe. The tourniquet which has long been used for this purpose is a length of stretchy rubber tubing which is passed about the upper arm and then knotted in place. This currently most popular tourniquet has a number of drawbacks, among which may be listed the possibility of disease transmission by reuse of the tourniquet near the sites of vein punctures, painful distortion of the skin by the knotting procedure, and injury by the inserted needle resulting from the jerk given to the tubing by a phlebotomist in attempting to release the knot after the needle has been inserted in a vein. Various other forms of tourniquets have been proposed in an effort to overcome at least the knotting problem, such tourniquets being reuseable and relatively expensive in terms of manufacturing costs. For example, in one such tourniquet, shown in U.S. Pat. No. 3,086,529, a pair of mating Velcro strips are sewn to respective ends of an elastic band. I am aware of no phlebotomist's tourniquet, other then the inexpensive length of flexible rubber tubing, which have enjoyed any significant measure of success or wide useage. The rubber tubing tourniquet remains to the present the most popular phlebotomist's tourniquet. A very inexpensive, throw-away or disposable tourniquet which can be easily used and which would avoid problems of disease transmission and trauma associated with the rubber tubing tourniquet is much to be desired.

SUMMARY OF THE INVENTION

The present invention relates to a disposable phlebotomist's tourniquet which comprises a supple, flat, elastic band which has bonded to one flat surface adjacent one end a non-stretchable pressure sensitive adhesive strip with a protective liner covering the adhesive strip during storage, the liner having a pull tab to facilitate peeling the liner away from the adhesive strip. The peel strength of the liner to the adhesive strip is less than the peel strength of the adhesive strip to the band so that when the liner is peeled away, the adhesive strip remains bonded to the band surface. The band is of a length permitting it, when stretched about the human upper arm, to have its ends well overlapped with a portion of the flat other surface of the stretched band coming into confronting relationship with the exposed adhesive surface of the adhesive strip and being bonded thereto to anchor the band in place about the arm. The non-stretchable adhesive strip and the surface of the band to which it is attached provide an adhesive surface of constant dimensions for receiving the confronting surface of the stretched band as the latter is wrapped around the arm.

DESCRIPTION OF THE DRAWING

FIG. 1 is a perspective view of a human arm showing the disposable tourniquet of the invention in place;

FIG. 2 is a perspective view of the disposable tourniquet of the invention with protective liner attached;

FIG. 3 is a partially broken away side view of the tourniquet of FIG. 2;

FIG. 4 is a cross sectional view taken along line 4—4 of FIG. 3; and

FIG. 5 is a partially broken away perspective view showing a portion of the tourniquet of the invention in stretched condition.

DETAILED DESCRIPTION OF THE PREFERRED EMBODIMENT

With reference to FIG. 2, the tourniquet of the invention is designated generally as 10, and includes a flat, elongated elastic band 12 having bonded adjacent one end 12.1 a substantially non-stretchable pressure-sensitive adhesive strip 14. The adhesive strip has its exposed adhesive surface covered with an easily removable liner 16 which may be a strip of plastic film or the like. One end 16.1 of the liner, desirably adjacent the end 12.1 of the band, protrudes beyond the adhesive strip to serve as a pull tab, the adhesive strip and liner being spaced inwardly slightly from the end 12.1 of the band so that the latter end can be gripped with fingers of one hand and the tab 16.1 may be gripped with the fingers of the other hand to permit the liner to be peeled away from the adhesive strip.

The band 12 is desirably a single length of inexpensive material such as latex rubber, plastic film, and the like. By "elastic" as used herein, reference is made to a material which may be stretched to a length greater than its original length and which also has the tendancy to return, at least slightly, toward its original length when stretching force is removed. Although only very slightly stretchable materials may be used for the band 12, it is desired that the band material be stretchable to a length of at least about 120 percent of its original length, and preferably 150 percent of its original length without breaking. It is the elasticity, as this term is used herein, of the band 12 which causes the tourniquet of the invention to be snuggly held about a human limb to cause veins distal of the tourniquet to stand out, and hence completely inextensible materials are not desirable for use as the band material. Bias-cut woven cloth, knit cloth, and fabric having elastic strings therethrough are other examples of materials suitable for use as the band 12. Desirably, however, the band is made from a non-woven material such as rubber or plastic. The length of the band in its unstretched state is such that when the band is stretched around the upper arm, the other end 12.5 of the band will completely overlap the adhesive strip 14, leaving the terminal portion of the other end 12.5 of the band hanging loosely as shown in FIG. 1. If an easily stretchable material, such as thin latex rubber sheeting, is employed as the band material, then the minimum length of the band can be relatively short; eg., 8 or 9 inches. If the band is of a material or thickness such that relatively great force is required to stretch the band, the minimum length of the band must be somewhat longer, eg., 15–20 inches. A band of latex rubber 14 inches in length with width and thickness dimensions of 1 inch and 0.020 inches, respectively, has yielded excellent results. Preferably, the length of the band is in the range of about 12 to about 16 inches. The band should additionally be of sufficient width so that when it is stretched and wrapped about the arm, the band has a sufficient area of surface-to-surface contact with the skin to avoid cutting into or otherwise bruising the flesh of the arm. A width of approximately 1 inch is desired, although slightly greater or lesser widths may also be employed. The thickness of the band, and the band material, should be such that the band itself is limp and drapable, rather than relatively stiff. When the band is stretchingly wrapped about the arm during use, the band should "cup" slightly so that a cross section of the band taken transversely of its length shows the band to be concave outwardly. The longitudinal edges of the band are thus prevented from digging into the flesh. The limpness, or drapability, associated with a latex rubber sheet 0.020 inches in thickness, or a highly plasticized polyvinylchloride film 0.002 inches in thickness, is appropriate for band materials of the present invention.

The adhesive strip 14 is desirably slightly narrower than the band 12 so that contact of the adhesive with the skin is avoided. In the embodiment referred to above in which a latex rubber band one inch in width was employed, an adhesive strip three-fourths of an inch wide and 2½ inches long provided very good results, the adhesive strip being centered adjacent the end 12.1 of the band so as to provide ⅛ inch margins between the longitudinal edges of the adhesive strip and the adjacent edges of the band. The adhesive strip is spaced slightly inwardly, eg. ¾ inches–1 inch, from the one end 12.1 of the band so that this end of the band may be grasped between the fingers without contacting adhesive. The adhesive strip is relatively non-stretchy, and may include an internal reinforcement such as a length of relatively inextensible plastic film. In the embodiment depicted in FIG. 4, the adhesive strip is of the construction designated collectively as 14 and includes an inner, non-extensible plastic film 14.2 sandwiched between two layers of pressure sensitive adhesive. The plastic film 14.2 may be polyester, cellophane, strong paper, or other material. Of importance is the fact that the stretchability, that is, the ease of stretching, of the adhesive strip must be less than that of the band 12. This feature permits the end of the tourniquet bearing the adhesive strip to assume the configuration shown in FIG. 5 when the tourniquet is stretched, the adhesive strip 14 and that section of the band to which the adhesive strip is bonded retaining constant dimensions whereas the band material itself has a tendancy to neck down as shown at 12.3 in FIG. 5.

The adhesive which is employed in the adhesive strip is of the pressure sensitive variety known to the adhesive art and employed in adhesive tapes such as surgical tapes. The adhesive should be readily adherent to the opposed flat surface of the band, and the adhesive bond which is formed during use of the tourniquet should have relatively high shear strength. Although hypoallergenic adhesives are desired, such adhesives are not critical to the invention since the adhesive itself does not touch the skin when the tourniquet of the present invention is correctly used. It is desired, however, that the adhesive be nontoxic and nonirritating to normal skin.

Over the outer, or exposed, layer of adhesive 14.3 is positioned a peel-away liner 16. The purpose of the liner is to protect the outer surface of the adhesive layer 14.3 during packaging and storage, and the liner 16 is stripped away and discarded just before the tourniquet of the invention is to be applied to the arm. The surface of the liner which contacts the adhesive layer 14.3 should adhere poorly to this adhesive layer so that when the liner is peeled away, the adhesive strip 14 in its entirety remains with the band 12. Silicone treated release paper has given excellent results, and other materials which may be used include various low-adhesion plastic films such as films of polyethylene, polytetrafluoroethylene (Teflon TFE, a product of the DuPont Company), etc. The force required to peel the liner from the adhesive strip 14 must be less than the force required for cohesive failure of the adhesive strip and must also be less than the force required to peel the adhesive strip from the band 12. Use may be made of various known coatings on the liner to decrease the adhesion between liner and adhesive, and various materials may be employed to increase adhesion between the adhesive strip and the band 12. Thus, a wide variety of adhesives and liners may be employed, and those skilled in the adhesive art will be able to readily select an appropriate adhesive and liner for use in the present invention.

A tourniquet of the invention may be made by hand, as by providing a length of latex rubber sheeting, applying to one end thereof the adhesive strip 14, and thereover applying the liner 16. The manufacture of tourniquets of the invention may readily be automated; for example, a roll of adhesive strip material approximately 2½ inches wide and having the construction shown in FIG. 4 may be provided with a continuous length of liner 16 along one adhesive surface with the edge of the liner protruding slightly from the side of the adhesive strip, the adhesive material thereafter being laminated to and along one edge of a length of band material having a width of approximately 14 inches. The resulting laminate may then be transversely cut into one inch lengths. Various other manufacturing methods will be apparent to the skill artisan.

In use, the pull tab 16.1 of the liner of a tourniquet of the invention is grasped between the fingers of one hand, with the terminal end 12.1 of the band being held by the other hand, and the pull tab is pulled backward to peel away the liner 16. The end 12.1 of the band is then pressed against the skin of the bared upper arm with one hand, while with the other hand the operator stretches the other end 12.5 of the band around the arm, the adhesive strip 14 being on the outside. When the band is stretched fully about the upper arm with the desired tightness, that portion of the surface of the band which comes into confronting relationship with the adhesive strip 14 is pressed against the strip, and the tourniquet is thus held in place. The end 12.5 of the tourniquet extends beyond the adhesive bond thus formed, and hangs loose as shown in FIG. 1. When a needle has been inserted into a vein distally of the tourniquet so that blood may be removed, then the tourniquet may be gently removed from the arm without jarring by simply pulling the end 12.5 of the band away from the arm gently, peeling apart the adhesive bond and permitting the tourniquet to fall loosely away from the arm. In this manner, little if any twisting or jerking motion is imparted to the arm which would result in injury to arm tissues by the needle. The tourniquet, being of very inexpensive material, can thereafter be discarded. If desired, the tourniquets of the invention may be rendered sterile before use by treatment with heat or a sterilizing gas.

Manifestly, I have provided a disposable tourniquet of inexpensive manufacture which reduces the possibility of disease transmission and which may be employed with minimal, if any, tissue damage of the type associated with the use of popular rubber tubing tourniquets.

While I have described a preferred embodiment of the present invention, it should be understood that various changes, adaptations, and modifications may be made therein without departing from the spirit of the invention and the scope of the appended claims.

What is claimed:

1. A disposable phlebotomist's tourniquet, comprising a single, flat, solid elastic band 8–20 inches in length, a non-stretchable, pressure-sensitive adhesive strip bonded to only one flat surface of the band adjacent but spaced from one end of the latter and having a pressure-sensitive adhesive surface, the adhesive strip including a non-extensible strip of sheeting therein to impart non-stretchability to the adhesive strip, the non-extensible strip and the surface of the band to which the strip is bonded coacting to resist deformation of the adhesive strip when the band is stretched, a removable protective liner covering the pressure-sensitive adhesive surface and having a peel strength to the adhesive strip less than the peel strength of the strip to the band, the liner having at one end a projecting tab to facilitate easy removal of the liner from the adhesive strip.

2. The tourniquet according to claim 1 in which the band is of latex rubber sheeting.

3. The tourniquet of claim 1 in which the band is of plasticized polyvinylchloride film.

4. The tourniquet of claim 1 in which the adhesive strip is spaced approximately three-fourths inches from one end of the band and extends longitudinally of the band for a distance of at least 2½ inches.

5. The tourniquet according to claim 1 in which the band is sufficiently supple to cup concavely outwardly when applied to and stretched about the flesh of the upper arm to apply gentle, non-cutting pressure to the flesh.

6. A disposable phlebotomist's tourniquet, comprising a single, flat, solid, supple, drapable elastic band approximately 1 inch in width and of 8–20 inches in length, a pressure-sensitive, relatively non-stretchable adhesive strip bonded to one flat surface of the band adjacent to but spaced from the edges of and from one end of the band and providing a pressure-sensitive adhesive surface readily adhereable to the opposed flat surface of the band, the adhesive strip including a strip of substantially non-stretchable sheet material sandwiched between layers of pressure-sensitive adhesive, one of the adhesive layers providing the bond between the adhesive strip and the band adjacent one end of the latter, a protective liner adhered to and protectively covering the other pressure-sensitive adhesive surface of the adhesive strip and having a peel strength to the adhesive strip less than the peel strength of the adhesive strip to the band to which it is bonded, the liner projecting beyond that end of the adhesive strip nearest the adjacent band end to define a graspable pull tab for peeling the liner from the adhesive strip, the non-stretchable adhesive strip coacting with that section of the band to which it is bonded to maintain substantially constant the dimensions of the pressure-sensitive adhesive surface to which a portion of the opposed flat surface of the band may be adhered when the band is stretched to encircle the arm.

7. The tourniquet of claim 6 in which the band is approximately 14 inches in length and in which the adhesive strip is approximately 2½ inches in length and is spaced approximately three-fourths of an inch from the one end of the band.

* * * * *